US00PP29951P2

(12) United States Plant Patent
Hansen

(10) Patent No.: US PP29,951 P2
(45) Date of Patent: Dec. 4, 2018

(54) ***PANICUM* PLANT NAMED TOTEM POLE**

(50) Latin Name: ***Panicum virgatum* (L.)**
Varietal Denomination: Totem Pole

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 15/732,457

(22) Filed: Nov. 15, 2017

(51) Int. Cl.
*A01H 5/12* (2018.01)

(52) U.S. Cl.
USPC ..... Plt./384

(58) Field of Classification Search
USPC ..... Plt./384
See application file for complete search history.

*Primary Examiner* — Annette H Para

(57) ABSTRACT

The new and distinct plant of ornamental switch grass named *Panicum virgatum* 'Totem Pole' with broad blue-green foliage that retains it coloration into the fall. The upright, columnar and dense culms produce tall plant with broadly-spreading airy panicles of tan seed heads that are retained into winter.

1 Drawing Sheet

Latin botanical classification: *Panicum virgatum* (L.).
Variety denomination: 'Totem Pole'.

BACKGROUND OF THE PLANT

*Panicum virgatum* 'Totem Pole', hereinafter also referred by just the cultivar name 'Totem Pole' and the "new plant" is a new and distinct cultivar of switch grass. The seed was collected by the inventor in the autumn of 2011 as an open pollinated selection from an isolation block of HK10-02 (not patented) and siblings of HK10-02 at a wholesale perennial nursery in Zeeland, Mich. The individual seedling was initially selected from among many for further observation in the summer and fall of 2013 at which time it was assigned the original breeder code H11-02-04.

The new plant has been successfully asexually propagated by division at the same wholesale perennial plant nursery in Zeeland, Mich. and found to produce stable and identical plants that maintain the unique characteristics of the original plant. The plant is stable and reproduces true-to-type in successive generations of asexual reproduction.

No plants of *Panicum virgatum* 'Totem Pole' have been sold in this country or anywhere in the world prior to the filing of this application, nor has any disclosure of the new plant been made prior to the filing of this application with the exception of that which was disclosed or sold within one-year period of the filing of this application and was either derived directly or indirectly from the inventor.

BRIEF SUMMARY OF THE PLANT

*Panicum virgatum* 'Totem Pole' differs from its female parent, HK10-02 in that the new plant is taller, has very broad, gray-green foliage and the light, airy, greenish-tan panicles cover the top two-thirds of the plant.

The nearest comparison variety known to the inventor is *Panicum* 'Blue Fountain' U.S. Plant Pat. No. 28,192. The new plant is similar in leaf color but shorter and more upright and columnar than 'Blue Fountain'. Compared with 'Thundercloud' U.S. Plant Pat. No. 20,665 the new plant is much shorter and more upright and columnar. The new plant is slightly taller than 'Dallas Blues' U.S. Plant Pat. No.

11,202 and does not develop any purplish foliage toward fall. Other similar switch grass comparison cultivars are succinctly exemplified in Table 1 below including:

TABLE 1

| CULTIVAR | U.S. PLANT PAT. NO. | TOTAL HEIGHT (cm) | INITIAL COLOR |
|---|---|---|---|
| 'Blue Fountain' | 28,192 | 210 | blue green |
| 'Cape Breeze' | 24,895 | 75 | dark green |
| 'Dallas Blues' | 11,202 | 193 | grayed blue green |
| 'Thundercloud' | 20,665 | 275 | blue green |
| 'Hot Rod' | 26,074 | 90 | blue green |
| 'Haense Herms' | (not patented) | 100 | green |
| 'Rostrahlbush' | (not patented) | 110 | green |
| 'Shenandoah' | (not patented) | 140 | blue green |
| 'Totem Pole' | current application | 200 | blue green |

| CULTIVAR | SEASONAL COLOR | SEASON OF CHANGE | HABIT |
|---|---|---|---|
| 'Blue Fountain' | blue green | early July | upright |
| 'Cape Breeze' | purple tipped | late September | compact upright |
| 'Dallas Blues' | purple tipped | late September | upright arching |
| 'Thundercloud' | blue green | none | arching upright |
| 'Hot Rod' | red purple | early spring | upright |
| 'Haense Herms' | red purple | early August | upright |
| 'Rostrahlbush' | red purple | early August | upright |
| 'Shenandoah' | red purple | late July | arching |
| 'Totem Pole' | blue green | none | columnar |

The following traits of *Panicum virgatum* 'Totem Pole', in combination, have been repeatedly observed in multiple generations of asexually propagated plants and distinguish the new plant from all other switch grass plants known to the inventor:

1. Broad blue-green foliage that retains its coloration into the fall.
2. Upright, columnar and dense culms producing tall plants.
3. Broadly-spreading airy panicles of tan seed heads that are retained into winter.

BRIEF DESCRIPTION OF THE DRAWINGS

The photographs of the new plant demonstrate the overall appearance of a three-year-old plant growing in an outdoor display garden and a two-year-old plant in the greenhouse in Zeeland, Mich., including the unique traits. The colors are as accurate as reasonably possible with color reproductions. Ambient light spectrum, source and direction may cause the appearance of minor variation in color.

DETAILED BOTANICAL DESCRIPTION

Figure 1:
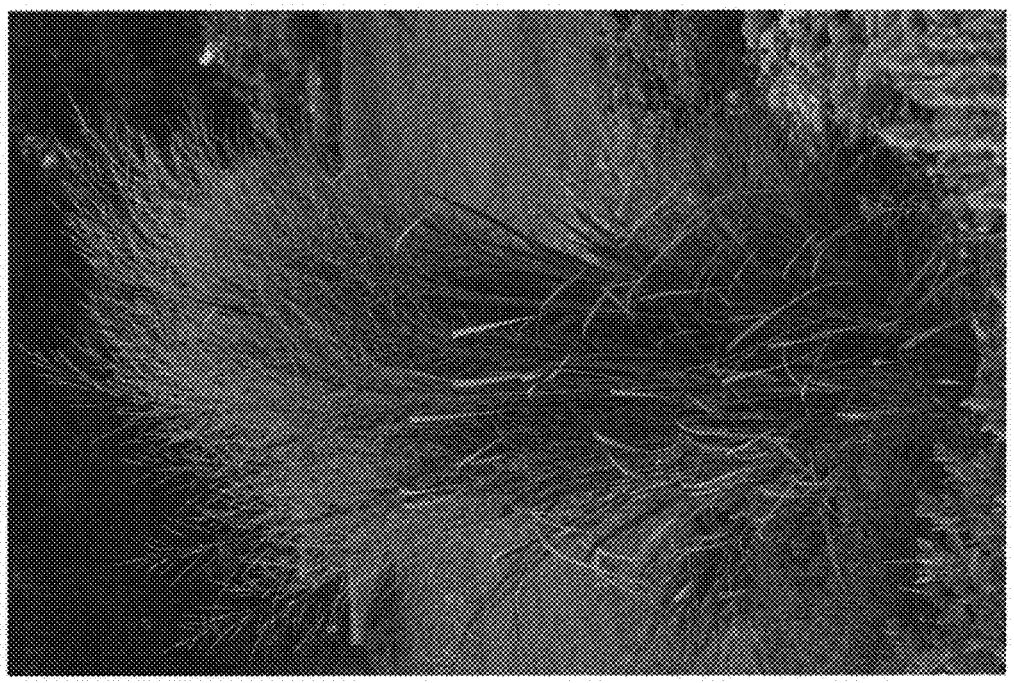
FIG. 1 shows the overall plant in mid-season.
Figure 2:
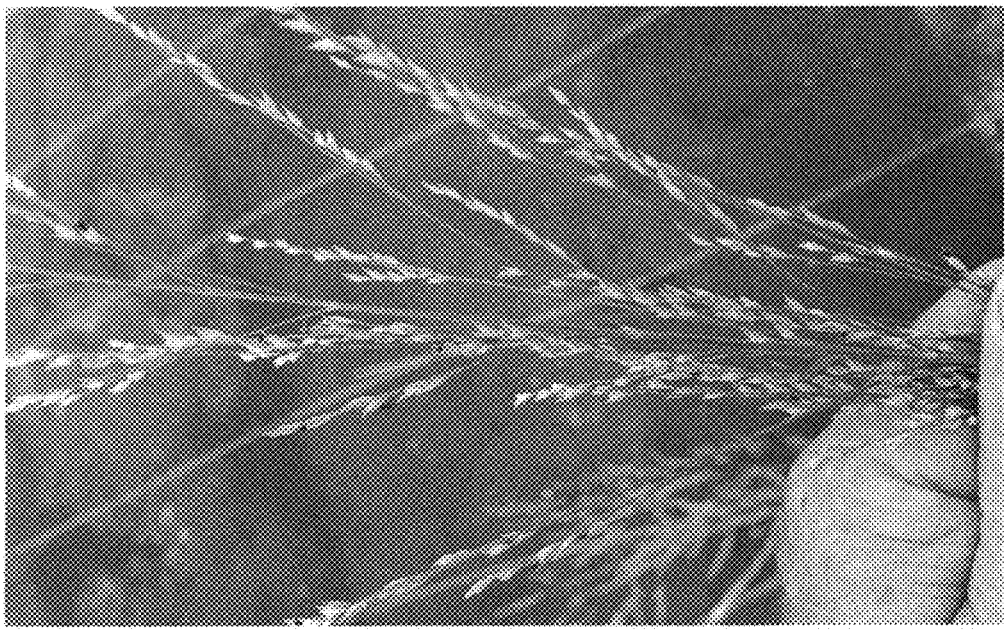
FIG. 2 shows a close-up of the inflorescence in late-July to early-August.

The following descriptions and color references are based on the 2001 edition of The Royal Horticultural Society Colour Chart except where common dictionary terms are used. The new plant, 'Totem Pole', has not been observed under all possible environments. The phenotype may vary slightly with different environmental conditions, such as temperature, light, fertility, moisture and maturity levels, but without any change in the genotype. The following observations and size descriptions are of a three-year-old plant in a loamy-sand trial garden of a wholesale perennial nursery in Zeeland, Mich., USA in full sun with supplemental water and fertilizer as needed.

Parentage: Female (seed parent) the proprietary hybrid *Panicum virgatum* HK10-02 (female) times open pollinated (male);

Propagation method: By division of the culms;

Time to finishing in a 3.8 liter pot: Rapid; about 7 to 9 weeks from 25 mm diameter plug;

Rooting habit: Normal, coarsely branching; root color nearest RHS 155D;

Plant description:

Plant shape and habit: Hardy herbaceous perennial forming tightly rhizomatous columnar clump, with very upright culms topped with finely-textured airy inflorescence producing a narrow clump about twice as tall as wide;

Plant size: Foliage height at flowering time is about 170.0 cm tall from soil line to the top of the foliage and 200.0 cm tall to top of flowers; about 25 cm wide at soil line and about 90.0 cm at widest point about 160.0 cm above soil;

Foliage description: Glabrous, glaucous; linear; flat; margin with microscopic marginal dentations; sheathed from node of attachment to ligule, adaxial and abaxial surfaces dull; deciduous but persist through winter;

Foliage size: To about 75.5 cm long and about 11.0 mm wide and about 52.0 cm long without sheath; averaging with sheath about 66.0 cm long and 10.0 mm wide; shorter at distal end; typically 6 leaves per culm;

Foliage color: Adaxial surface nearest RHS 189A; abaxial surface nearest RHS 189A; winter adaxial surface between RHS 165C and RHS 164B; winter abaxial surface between RHS 165C and RHS 164B;

Veins: Parallel; midrib about 0.5 mm across; abaxial ridged, adaxial slightly recessed;

Vein color: Adaxial midrib color proximal one-third between RHS 148B and RHS N138D, proximal on-third abaxial midrib nearest RHS N138D, distal two-thirds of midrib and secondary veins same color as the surrounding leaf on both adaxial and abaxial;

Culm (stem): Erect, terete, glabrous, glaucous, dull surface, 75% enclosed by leaf sheath, about six nodes per culm; about 90 culms per clump;

Culm dimension: To about 160.0 cm long without panicle, average about 150.0 cm; including panicle to about 200.0 cm long, average about 185.0 cm long; about 6.0 mm diameter at base; internode length average about 24.5 cm;

Culm color: Base nearest RHS N186C with undertone of between RHS 148C and RHS N138C; mid-section nearest RHS 188C with undertone of between RHS 138A and RHS 138B; top portion nearest RHS 189B;

Node description: About 6 per culm, slightly swollen to about 6.5 mm diameter;

Node color: Nearest RHS 164B;

Flower description: Finely-branched open panicle, one panicle per culm;

Flower timing: Beginning late July, flowering through late August, panicles dry and remain effective through winter; No flower fragrance detected;

Panicle: Pyramidal, about 47.0 cm long and 22.0 cm wide; overall effective color nearest RHS 189A;

Rachis: Terete, branched, glabrous, glaucous; about 47.0 cm long and about 3.0 mm at base; branches to about 27.5 cm long and about 1.0 mm diameter held at about 60 degree angle above horizontal; color nearest RHS N138C;

Spikelet: Usually with two florets; about 10.0 mm long;

Rachilla: Thin, terete, stiff; about 7.0 mm long and about 0.2 mm diameter; color nearest and RHS N138C;

Lower glume: About 2.5 mm long and 1 mm wide; without awn; color between RHS 191B and RHS 191A;

Lemma: Without bristle or short bristle; acute apex, truncate base; margin entire; upper and lower both about 3.0 mm long and 0.5 mm wide; color nearest RHS 139D;

Palea: Acute apex, truncate base, margin entire; about 2.0 mm long and 0.7 mm across; transparent;

Gynoecium: Two;

*Stigma*.—Two, plumose, protruding about 1.5 mm from glume and about 0.5 mm diameter; color nearest RHS 165A.

*Style*.—Thin; about 1.0 mm long and 0.1 mm diameter; color nearest RHS 155D.

*Ovary*.—Ellipsoidal; acute apex, rounded base; about 2.5 mm long and 1.0 mm diameter; color between RHS 14RA and RHS 148B.

Androecium: two or three;

*Filaments*.—Short; hair-like; less than 0.1 mm diameter and up to 1.0 mm long; color nearest RHS NN155D.

*Anthers*.—Two; dorsifixed, longitudinal; about 2.5 mm long and about 1.0 mm wide; color nearest RHS N163A.

*Pollen*.—Round, abundant; less than 0.1mm in diameter; nearly transparent, color lighter than RHS 155D.

Fruit: Caryopsis; about 2.5 mm long and about 1.0 mm wide; color between RHS 199D and RHS 161C;

Hardiness, pest and disease resistance: The plant is very drought once established. Hardiness at least from USDA zone 4 through 9. Disease and pest resistance beyond what is typical of that of other switch grasses has not been observed.

I claim:

1. A new and distinct cultivar of ornamental switch grass plant named *Panicum virgatum* 'Totem Pole' as herein described and illustrated.

* * * * *